United States Patent [19]

O'Brien

[11] Patent Number: 5,059,909

[45] Date of Patent: Oct. 22, 1991

[54] DETERMINATION OF PARTICLE SIZE AND ELECTRICAL CHARGE

[75] Inventor: Richard W. O'Brien, Turramurra, Australia

[73] Assignee: Colloidal Dynamics Pty. Ltd., Sydney, Australia

[21] Appl. No.: 328,254

[22] PCT Filed: Sep. 30, 1987

[86] PCT No.: PCT/AU87/00333

§ 371 Date: Feb. 27, 1989

§ 102(e) Date: Feb. 27, 1989

[87] PCT Pub. No.: WO88/02482

PCT Pub. Date: Apr. 7, 1988

[30] Foreign Application Priority Data

Sep. 30, 1986 [AU] Australia ............................ 8241/86

[51] Int. Cl.$^5$ ...................... G01R 29/12; G01N 29/02
[52] U.S. Cl. .................................... 324/457; 324/453; 324/71.1; 73/587
[58] Field of Search ...................... 324/71.1, 452, 453, 324/457; 73/584, 596, 602, 592, 587, 589

[56] References Cited

U.S. PATENT DOCUMENTS

| 4,497,208 | 2/1985 | Oja et al. | 73/584 |
| 4,633,714 | 1/1987 | Mazumder et al. | 73/596 |
| 4,679,439 | 7/1987 | Culkin | 324/71.1 |

Primary Examiner—Jack B. Harvey
Attorney, Agent, or Firm—Blum Kaplan

[57] ABSTRACT

A method for the determination of particle size and electric charge or zeta potential of particles dispersed in a fluid medium. The particle size and charge are determined from measurements of (1) the phase lag between an applied alternating electric field and the resulting particle velocity, and (2) the amplitude of the particle velocity. Also disclosed is the measurement of the interaction of sound waves and electric fields in the fluid medium over a range of frequencies to obtain the particle size and zeta potential.

10 Claims, 1 Drawing Sheet

DETERMINATION OF PARTICLE SIZE AND ELECTRICAL CHARGE

The present invention relates to a method of and means for the determination of particle size and electric charge or zeta potential in a colloidal system.

A colloid is a suspension of small particles in a fluid medium (e.g. aerosols and the dispersions of solids in liquids). Colloids have great scientific and industrial importance. Examples include blood, paints, slurries and milk.

The most significant characteristics of many colloidal systems are the size and charge of the particles, since most other properties of the system are influenced to some extent by these factors.

There are many areas of industry in which it is necessary to be able to determine the size of particles suspended in a liquid or the electric charge on the particles. For example, in the mining industry, mineral ores must be ground down until the particles are the right size for floating, and in liquid purification processes it is important to be able to keep particle charge low in order to encourage the coagulation of the particles into clumps large enough to be filtered out.

In nearly every colloidal system the particle carries an electric charge. This charge is balanced by an excess of ions of opposite charge in the suspending liquid. These ions tend to cluster around the particle, forming a diffuse cloud which is known as the double-layer. The voltage difference between the particle surface and the liquid beyond the double-layer in equilibrium is referred to as the "zeta potential" denoted by $\zeta$. The bigger the particle charge, the bigger the $\zeta$ potential.

BACKGROUND ART

Known methods for measuring particle size include the use of electron microscopes, Coulter counters, centrifuges and dynamic light-scattering devices. However, all of these known methods require the removal, and subsequent dilution of the sample prior to testing, making such methods unsuited to on-line monitoring of particle size.

Known methods for measuring particle charge all involve the measurement of the particle velocity in an electric field. In some methods, the velocity is determined by measuring the time required for the particle to pass between two points on a microscopic grid when a steady electric field is applied. In other methods, particle velocity is measured by a light-scattering technique with an alternating electric field of 10 or 20 Hz.

There is apparatus suitable for determining both particle size and charge. The "Zeta Sizer" (Malvern Instruments) measures the light scattered from a laser beam as it passes through the suspension. In the absence of an applied field, the fluctuations in the scattered light provide information about the particle size, and if a slowly varying electric field is applied the particle charge can be obtained from the fluctuating light signal.

All of the above methods suffer the disadvantage that they require sample dilutions and most require use of light-scattering instruments. Accordingly, opaque samples cannot be measured.

DISCLOSURE OF THE INVENTION

It is an object of the present invention to provide a method of and means for the determination of particle size and electric charge or zeta potential of particles in a colloidal system.

It is another object of the present invention to provide a method of and means for the determination of particle size and electric charge or zeta potential of particles in a colloidal system on-line and without sample dilution, even in opaque solutions.

It is a further object of the present invention to provide a method of and means for determination of the motion of colloidal particles in a high-frequency field, for it is by the use of high frequency measurements of particle motion that the particle size and charge can be determined.

These and other objects of the present invention will be apparent from the following non-limiting disclosure of the invention.

According to one aspect of the present invention there is provided means for determining the size and charge of particles dispersed in a fluid medium from the phase lag and amplitude of particle velocity in an alternating electric field.

According to a further aspect of the present invention there is provided means for determining the particle size in a fluid medium having uniform, low $\zeta$ potential from a measurement of the phase of the particle motion in a high frequency alternating electric field, and wherein the zeta-potential can be determined from the amplitude of the motion in the alternating field.

According to another aspect of the invention there is provided a means for determining the particle motion in an alternating field from measurements of the interaction of sound waves in the suspension.

According to a further aspect of the invention there is provided means for measuring and generating the interaction of sound waves and electric fields in a suspension, comprising positioned spaced apart electrodes and pressure transducers in contact with the suspension, enabling the simultaneous measurement of electric current, potential, and pressure differences in the suspension.

These and other aspects of the invention will be apparent from the above, and from the following description relating to the invention.

BRIEF DESCRIPTION OF THE DRAWINGS

The invention will be further described with reference to the drawings, in which.

MODE FOR CARRYING OUT THE INVENTION

Figure 1:
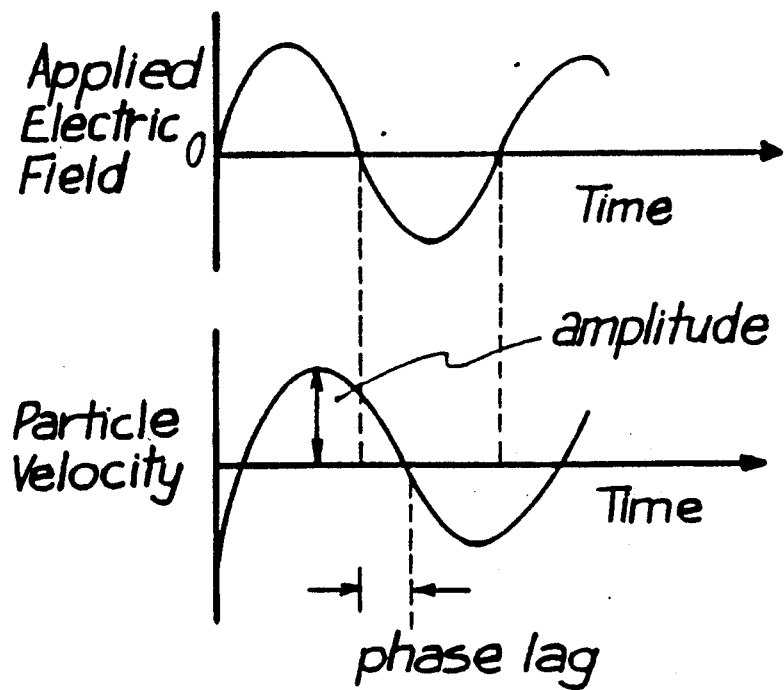
FIG. 1 illustrates separate graphs of applied electric field versus time and particle velocity versus time.

When an alternating electric field is applied to a colloidal suspension it causes the particles to oscillate at the frequency of the applied field in a way which depends on particle size and zeta potential. If the frequency of the applied field is much lower than the optimum sizing frequency (to be defined hereinafter), the particle velocity will be in phase with the applied field; i.e., when the field switches direction, so too does the particle motion. At higher frequencies a phase lag develops, i.e., there is a time lag between the change in direction of the applied field and the subsequent change in the direction of the particle motion due to the particle inertia. This is illustrated in FIG. 1.

For a given particle, the phase lag increases with particle radius (since this increases the particle inertia), while the velocity amplitude decreases with radius. In general these two quantities also depend on particle $\zeta$ potential. Thus by measuring phase lag and amplitude it should be possible to determine size and charge.

For suspensions in which the particles have a uniform, low $\zeta$-potential it is shown that the phase lag is independent of the magnitude of $\zeta$. For such suspensions a measurement of phase lag can therefore be used to determine particle size, and the amplitude measurement can then be used for charge determination. Mathematical formulae relating phase lag to particle size, and amplitude to size and charge are presented for a dilute suspension of spheres with low $\zeta$. The particle velocity can be obtained indirectly from measurements involving the interaction of electric fields and sound waves in the suspension. It can for example be obtained for the measurement of sound waves generated by electric fields, or from the measurement of electric fields generated by sound waves in the suspension. An advantage of the present invention is that measurement can be performed on-line, as opposed to the sampling methods required of the prior art and it can be applied to opaque suspensions. The present invention can also be applied to larger particles than can the prior art light scattering techniques, which are limited to <1 $\mu$m range. In the case of highly charged particles, it may be necessary to reduce the charge by the addition of salt or acid/base, since the determination of size and charge is simpler for systems with low $\zeta$-potential. Alternatively, high $\zeta$ systems can be sized by using a prior calibration procedure.

The only theoretical studies of particle velocity that have appeared in the literature have been concerned with either a steady electric field ("Zeta Potential in Colloid Science" by R. J. Hunter, Academic Press 1981, Chapter 3) or an alternating field at frequencies which for most suspensions are well below the optimum frequency for size determination (Hinch E. J., et al, J. Chem. Soc. Faraday Trans. 2 80, 535 (1984)). The latter authors made no mention of the possibility of size determination from phase lag and amplitude measurement.

In accordance with the present invention particle velocity has been calculated for a dilute suspension over the frequency range which is best-suited to particle sizing, that is frequencies of the order of $\nu/a^2$, where $\nu$ is the kinematic viscosity of the suspending liquid (=0.01 cm$^2$/sec for water), and a is the particle radius. For an 0.1 $\mu$m radius particle, this optimum frequency is 16 MHz. In this frequency range the phase lag is a sensitive function of frequency, and for this reason it is well-suited for determining particle sizes.

As indicated above, the particle velocity can be determined by measuring the interaction of sound waves and electric fields in the suspension; it can for example be determined by measuring sound waves generated by an alternating electric field, and by measuring the electric fields generated by sound waves. Of these two effects, only the second has appeared in the scientific literature. Most of the work on this effect is restricted to electrolytes, with the most notable exception being two papers by J. A. Enderby (Proc. Roy. Soc. A 207, 329 (1951)) and J. A. Enderby and F. Booth (Proc. Phys. Soc. 65, 321 (1952)). These authors apparently had no idea that this effect was related to the particle velocity. Furthermore, there appear to be a number of errors in their work R. W. O'Brien, J. Fluid Mech. (to be published). There is no disclosure in these references of the possibility of obtaining particle size from this effect.

The phenomenon of sound wave generation by an electric field is described in U.S. Pat. No. 4,497,208. However, there is no disclosure in the above referenced patent of the link between the effect and particle velocity, or of the possibility of determining particle size from the effect.

Formulae associated with particle size and charge determination

There are two main aspects to this invention:

(1) A method for determining particle size and charge from measurements of particle velocity in an alternating electric field (2) A method for obtaining that particle velocity from measurements of the interaction of sound waves and electric fields in the suspension.

With the aid of these procedures it is possible to determine particle size and charge from measurements of the interaction of sound waves and electric fields in any suspension.

Aspect (1) of the invention will be described in the following two sections. Aspect (2) will be addressed in section 3.

1. The velocity of an isolated sphere in an alternating electric field.

In a dilute suspension, each particle can be treated as being alone in an infinite liquid. In this section a dilute suspension of uniform spheres will be studied. We let $E_o \cos wt$ denotes the ambient electric field in the suspension; this is the electric field which would apply in the absence of any particles. $|E_o|$ is the amplitude of this applied field, and $w/2\pi$ is the frequency.

Following the standard procedure for problems involving sinusoidally varying quantities, this applied field can be rewritten as $\underline{E}_o e^{iwt}$, with the understanding that the field is actually given by the real part of this complex expression.

Since colloidal particles are electrically charged, the applied field exerts an alternating force on the particles which causes them to oscillate backwards and forwards at the frequency of the applied field. The particle velocity is denoted by $\underline{V}_o e^{iwt}$. The complex quantity $\underline{V}_o$ requires two real numbers (and a direction) for its specification. The two numbers are $|\underline{V}_o|$, the amplitude of the particle velocity, and arg $\underline{V}_o$ the phase lag referred to earlier.

The quantity $\underline{V}_o$ is proportional to $\underline{E}_o$, the strength of the applied field. For spherical particles, which on account of their symmetry move in the direction of the applied field, this proportionality relation takes the simple form $$\underline{V}_o = \mu \underline{E}_o \qquad (1)$$

The phenomenon of particle motion in an electric field is called "electrophoresis", and $\mu$ is termed the "electrophoretic mobility" of the particle. Like $\underline{V}_o$, $\mu$ is a complex quantity. $|\mu|$ is equal to $|\underline{V}_o|$ for unit applied field, and arg $\mu$ is equal to the phase lag. Since $\mu$ is independent of $\underline{E}_o$, it can only depend (for any given frequency) on the properties of the particle and solvent; $\mu$ is the quantity which should be measured in the course of determining particle size and charge.

The calculation of $\mu$ is greatly complicated by the fact that the applied field distorts the double layer. As a result the double layer ions impose an electric force which retards the particle, thereby affecting both the phase lag and the amplitude of the motion. Fortunately, at the optimum sizing frequency, this double-layer distortion can be neglected in the important case of particles with low $\zeta$ potential.

The range of validity of this low-$\zeta$ approximation depends on the ratio of particle radius to double-layer thickness. If the ratio is around one, the approximation should be valid for $\zeta$ potentials of up to about 50 mv. If particle radius is much greater than double-layer thickness, the $\zeta$ potential limit will be larger. For example, if the ratio of the radius to thickness is 50, the low-$\zeta$ approximation will work up to about 100 mv. This should cover most commonly occuring colloids. For the highly charged colloids it may be necessary to add salt or acid/base to reduce the $\zeta$ potential and thereby take advantage of the low-$\zeta$ results.

For a sphere with low $\zeta$, we have shown that the electrophoretic mobility is given by the formulae $$|\mu| = \frac{4\pi\epsilon}{3} |\zeta||G|, \quad (2)$$

$$\arg \mu = \pi(u(\zeta)-1)+\arg G, \quad (3)$$

where $$G = \kappa^2 a e^{\kappa a} \left(\frac{V'}{F'}\right)\left\{\frac{3e^{-\kappa a}}{\kappa}\left[a + \frac{1}{\kappa}\right] - \frac{6bc}{a}E_5(\kappa a) + \right. \quad (4)$$

$$2a\left|\frac{-ik}{ik-\kappa}e^{(ik-\kappa)a} + ca^3\left(\frac{ik}{a^2}E_3(-ika+\kappa a) - \right.\right.$$

$$\left.\left.\frac{3}{a^3}E_4(-ika+\kappa a) + \frac{3}{ika^4}E_5(-ika+\kappa a)\right)\right|\right\}.$$

Here
$E_n$ is the exponential integral
$\epsilon$ is the permittivity of the suspending liquid,
$\zeta$ is the "zeta potential" of the particle, a quantity related to its charge (see, e.g. chapter 2 of "Zeta Potential in Colloid Science" by R. J. Hunter, Academic Press, 1981),
$k-1$ is the double-layer thickness (related to the electrolyte concentration; see above reference),
a is the particle radius,
$V'/F'$ is the speed at which an uncharged sphere moves when acted on by an alternating force of unit magnitude, given by $$V'/F' =$$

$$\left|\pi\rho a^3 w\left\{\frac{6\nu}{wa^2} + \frac{2i}{3}\left(3 + \frac{2\Delta\rho}{\rho}\right) + 3\sqrt{2}(1+i)\sqrt{\frac{\nu}{wa^2}}\right\}\right|^{-1}$$

$\rho$ is the density of the suspending liquid,
$\nu$ is the kinematic viscosity of the suspending liquid, and
$\rho + \Delta\rho$ is the particle density.

Finally, the quantities k, a, b and c are defined by $$k = (i-1)\sqrt{\frac{w}{2\nu}},$$

$$a = \frac{-3a}{2ik}e^{-ika},$$

$$b = -\frac{a^3}{2}\left(1 - \frac{8}{ika} - \frac{3}{k^2a^2}\right),$$

and $$c = \frac{1 - iw'(1 - \epsilon_p/\epsilon)}{2 - iw'(2 + \epsilon_p/\epsilon)}$$

$\epsilon_p$ being the particle permittivity, and $$w' = w\epsilon/K^\infty,$$

where
$K^\infty$ is electrolyte conductivity.

Finally, $u(\zeta)$ is a function which is 0 when $\zeta<0$, and 1 for $\zeta>0$.

In the case when $ka>>1$ (thin double layer), equation (4) reduces to $$G = 3a\frac{V'}{F'}(1 - ika)(1 + c). \quad (6)$$

Since $(u(\zeta)-1)$ depends on the sign, but not on the magnitude of $\zeta$, and G is independent of $\zeta$, it follows from equation (3) that the phase lag arg $\mu$ is also independent of the magnitude of $\zeta$. This property of the phase lag makes it ideal for the determination of particle size. To illustrate this point reference is made to FIG. 2 wherein arg $\mu$ for the $ka>>1$ case has been plotted as a function of the non-dimensional variable $wa^2/\nu$.

Figure 2:
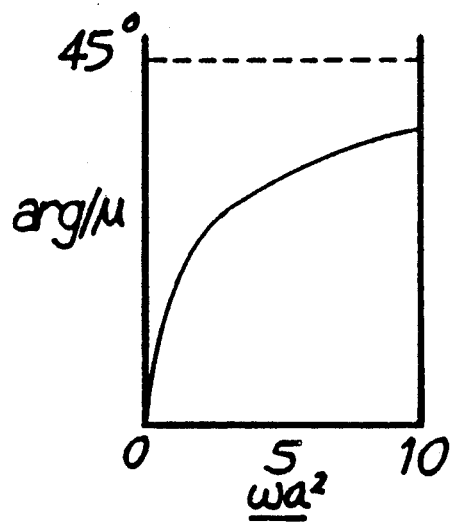
FIG. 2 illustrates graphically the determination of particle size from phase lag measurement.

FIG. 2 was constructed using equation (6) with parameters $\Delta\rho/\rho=1$, $\epsilon_p/\epsilon=0$, and $\zeta>0$.

From this figure it can be seen that for fixed values of w and $\nu$, arg $\mu$ increases monotonically with increasing particle radius, tending to a limiting value of 45° as $wa^2/\nu \rightarrow \infty$.

with the aid of this curve it is possible to obtain a unique particle size from any measurement of arg $\mu$. For example a phase lag of 14° implies that $wa^2/\nu=1$. If the suspending liquid is water, which has a $\nu$ value of 0.01 cm$^2$/sec, and if the frequency of the applied field is 1 MHz, the particle radius corresponding to $wa^2/\nu=1$ is 0.4 $\mu$m.

For a given solvent, the range of particle sizes which can be accurately measured in this way depends on the frequency of the applied field. From FIG. 2 it can be shown that a one degree error in the measurement of arg $\mu$ leads to a relative error of less than 6% in the assessed particle size provided $$1 < wa^2/\nu < 4.$$

Thus for any particle size, there is an optimum frequency range for size determination, given by $$\nu/a^2 < w < 4\nu/a^2.$$

Although the curve in FIG. 2 is only valid for a very limited class of suspension, the notion of an optimum frequency range is likely to have universal application. The precise end points of the range may vary from one suspension to the next, but the optimum will always be around $\nu/a^2$. For an 0.1 μm particle in water $\nu/a^2$ corresponds to a frequency of 16 MHz, while for a 1 μm particle, this frequency is 160 kHz.

From equation (3) it can be seen that arg μ changes by $\pi$ radians (corresponding to 180° in phase lag), as the $\zeta$ potential changes sign. Thus the curve of arg μ for $\zeta<0$ would have the same form as FIG. 2, but with arg μ reduced by 180° C. Since the total variation in arg μ with particle radius is only 45°, there is no possibility of a positive and a negative particle yielding the same phase angle.

In fact the sign of $\zeta$ can be immediately ascertained from the quadrant in which the phase angle lies: the first quadrant indicates $\zeta>0$, while the third quadrant implies $\zeta<0$.

Figure 3:
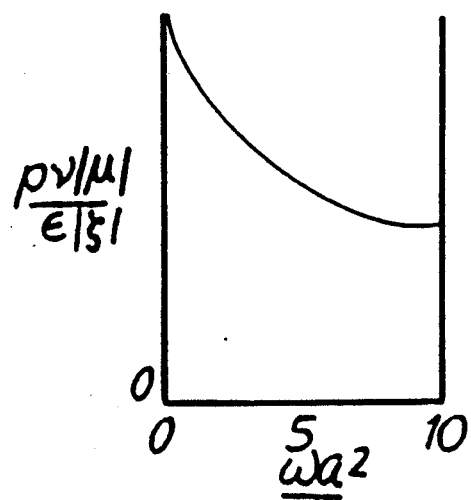
FIG. 3 illustrates graphically the subsequent determination of particle charge from amplitude measurement.

Once the radius a and the sign of $\zeta$ have been ascertained from the phase lag, $|\zeta|$ can be determined from the measured value of $|\mu|$. FIG. 3 shows the variation of the non-dimensional quantity $\rho\nu|\mu|/\epsilon|\zeta|$ with $wa^2/\nu$.

Once again the curve comes from equation (6), with the same parameters as in FIG. 2. From the curve it can be seen that $|\mu|$ decreases monotonically with increasing frequency or particle radius. This curve can be used for determining $|\zeta|$. For example, if the particle radius has been found to be 0.4 μm then from the figure $\rho\nu|\mu|/\epsilon|\zeta|=0.87$. If the measured $|\mu|$ is $3.5\times10^{-4}$ cm$^2$V$^{-1}$s$^{-1}$, it follows that $|\zeta|=50$ mv (assuming $\rho$, $\nu$ and $\epsilon$ values for water). Since the phase lag measurement indicated a positive $\zeta$, it is found that $\zeta=50$ mv.

Although FIGS. 2 and 3 were obtained with the formula (6) for the thin double layer case, the procedure herein described is valid for arbitrary double layer thickness. To summarize the main points:

(1) The particle size and the sign of $\zeta$ can be obtained from phase lag measurement.

(2) $|\zeta|$ can then be obtained from the measured $|\mu|$ value.

(3) The optimum sizing frequencies are around $w=\nu/a^2$.

2. Results valid for more general suspensions

The formula (1) defining the electrophoretic mobility can also be applied to a much more general class of suspensions, namely "statistically isotropic" suspensions. These are suspensions which appear to be isotropic, from the macroscopic point of view (Batchelor, G.K., J. Fluid Mech., 41, 545, (1970)). Many suspensions fall into this category, particularly if they have not been subjected to a flow and if sedimentation is not too significant.

Since these isotropic suspensions may be concentrated, the particle interactions will cause the velocity to vary from one particle to the next. The quantity $V_o$ which appears in equation (1) in this case is intended to represent an average of the particle velocities given by $$V_o = \sum_{j=1}^{N} v^j \Delta m^j / \sum_{k=1}^{N} \Delta m^k$$

where $v^j e^{iwt}$ is the velocity of the centre of mass of the jth particle in the sample, and $\Delta m^j$ is the particle mass minus the mass of solvent displaced by the particle.

The applied field $E_o$ also represents an average, namely an average of the local electric field over a representative volume of the suspension (see the previous reference). For a dilute suspension this is equivalent to the previous definition.

The notion of electrophoretic mobility is considerably more complicated for "non-isotropic" suspensions. In these suspensions the velocity $V_o$ is not usually parallel to the applied field. Thus if the applied field is parallel to the x axis of some cartesian coordinate system, the particle velocity will in general have components along the x,y and z axes. Since the velocity is still proportional to field strength, it is possible to define three electrophoretic mobilities, one for each component of $V_o$. Three more components are required to characterize the mobility with a field in the y direction, and another three for a field in the z direction, giving nine in all.

It is convenient to regard these nine mobilities as the components of a single entity known as the "electrophoretic mobility sensor", denoted by $\underline{\mu}$. The nine components of $\underline{\mu}$ are usually set out in the $3\times3$ matrix $$\begin{vmatrix} \mu_{11} & \mu_{12} & \mu_{13} \\ \mu_{21} & \mu_{22} & \mu_{23} \\ \mu_{31} & \mu_{32} & \mu_{33} \end{vmatrix},$$

where $(\mu_{11}, \mu_{21}, \mu_{31})$ E are the x, y and z components of $V_o$ caused by a field along the x-axis. The other two columns of the matrix give the velocity due to fields in the y and z directions respectively.

In this notation, the relationship between $V_o$ and $E_o$ for a non-isotropic suspension takes the compact form $$V_o = \underline{\mu} E_o$$

In the case of an isotropic suspension, the off-diagonal entries in the $\underline{\mu}$ matrix are zero, and the diagonal entries take the common value denoted earlier by μ. The above result reduces to (1) in this case.

The components of $\underline{\mu}$ will depend on the particle size and charge distribution. Unfortunately the exact calculation of this relationship is only feasible at present for dilute suspensions of particles of simple geometry. For the more complicated types of suspensions which are likely to be encountered in practice, there appear to be two options for obtaining approximate relations between size, charge and mobility.

(a) Cell Models

If the particles are not elongated or flat it should be possible to approximate them by spheres. In a cell model the effect of neigbouring particles on any given sphere is assumed to be the same as an outer spherical surface centred on that particle. The "cell" then consists of a single particle surrounded by a concentric spherical surface, with the annular region between occupied by electrolyte. Such models have been successfully used in the calculation of average sedimentation velocities (see "Low Reynolds Number Hydrodynamics" by Happel and H. Brenner, Prentice-Hall, (1965)) and in the calculation of electrophoretic mobilities (Levine S. and Neale G., J. Colloid. Interface Sci. 47, 520 (1974)) in steady electric fields, for concentrated suspensions. The boundary conditions to be applied at the outer surface of the cell depend on the problem at hand. The boundary conditions suggested here are: zero total force, zero pressure, zero perturbation in ion densities, and an electric potentional equal to $-E_o \cdot x$, where $x$ is the position vector measured from the particle centre.

These boundary conditions may require some modification in the light of future experimental studies.

(b) An empirical approach

If the cell model is not appropriate for the suspension of interest, an empirical approach can be adopted. In this approach, samples of the suspension are removed and analysed after each set of mobility measurements is made. These mobility measurements should be carried out over a range of frequencies spanning the optimum range corresponding to the expected particle size range. Changes in the particle size or $\zeta$ potential distribution can then be correlated with the form of the curves of $|\mu_{ij}|$ and arg $|\mu_{ij}|$ as a function of frequency, where the symbol $\mu_{ij}$ denotes any measured component of the mobility tensor.

For suspensions in which the $\zeta$-potential is both uniform and small, $\underline{\mu}$ will be proportional to $\zeta$. As a consequence the quantities arg $\mu_{ij}$ will be independent of the magnitude of $\zeta$, as we saw in the dilute suspension of spheres in §1. Although arg $\mu$ may depend on $|\zeta|$ for more general suspensions, it is still likely that of the two quantities $|\mu|$ and arg $|\mu|$, the latter will be the more sensitive function of particle size. Thus in attempting to correlate mobility with particle size distribution, attention should be focussed on arg $\mu$ rather than $|\mu|$.

3. The experimental determination of the electrophoretic mobility

Turning now to the second major aspect of the invention: the means by which the electrophoretic mobility can be measured experimentally.

In this section there is described a general class of devices which can be used for making these measurements, and how the mobility can be determined from the various measured quantities.

The results given in this section apply to any colloid, except in those instances where statistically isotropic colloids are specifically referred to.

The devices for measuring the mobility consist of a "cell" which contains the suspension, together with various means for measuring voltage differences (or electric currents) and pressure differences across the cell, and means for generating sound waves and/or alternating electric fields in the cell.

To take a simple example, the cell could consist of two parallel metal plates with the suspension filling the gap between them. Later in this section it will be shown how the mobility can be determined for such a cell from the measurement of the pressure difference and open circuit voltage difference generated between the plates by the vibration of one of those plates.

As may be gathered from the above description, the electrophoretic mobility is measured when both sound waves and electric fields are present in the suspension. In addition to its effect on particle motion, the electric field generates electric currents in the suspension. The sound waves also generate electric currents, due to the fact that both particles and solvent carry a charge, and the particle motions in the sound wave are different from that of the liquid, owing to the particle inertia. The total current density due to the electric field and the sound waves is given by an expression of the form $$i_o = \underline{\alpha} \nabla p_o + \underline{K}^* \underline{E}_o, \tag{6}$$

Here $i_o e^{iwt}$ is the volume-averaged current density, a quantity which includes both free charge and electric displacement contributions (see O'Brien, R.W., Adv. Coll. Interface Sci., 16, 281, (1982)). $\nabla p_o e^{iwt}$ is the macroscopic pressure gradient due to the sound waves, and $\underline{\alpha}$ and $\underline{K}^*$ are properties of the suspension, $\underline{K}^*$ being called the "complex conductivity tensor". Equation (6) has not appeared before in the scientific literature.

The quantity $\underline{\alpha}$, which characterizes the current due to the sound waves, is related to the electrophoretic mobility tensor by the formula $$\underline{\alpha} = \frac{\phi \Delta \rho}{\rho} \underline{\mu}^T, \tag{7}$$

where $\phi$ is the volume fraction of the suspension occupied by particles, and as before $\rho$ is the solvent density, and $\rho + \phi \Delta \rho$ is the suspension density: $\underline{\mu}^T$ is the "transpose" of the mobility tensor, the quantity whose components are obtained by interchanging the rows and columns of the $\underline{\mu}$ matrix.

With the aid of (7) it is possible to determine $\underline{\mu}$ once $\alpha$ is known. The devices described here determine $\underline{\mu}$ by measuring $\underline{\alpha}$.

Figure 4:
FIG. 4 illustrates a parallel plate cell used in obtaining measurements in some embodiments of the present invention.

In order to provide examples of ways is which $\mu$ can be measured using this class of device, reference is made to the parallel plate cell, illustrated in FIG. 4.

The separation h between the plates is assumed to be much smaller than the width and height of the plates. Sound waves are set up in the device by the forced oscillation of one of the plates. The resulting pressure difference across the plates $\Delta P e^{iwt}$ is measured by, for example transducers on the plates, and the open circuit voltage difference $\Delta \psi e^{iwt}$ is also measured.

In such a device the current $i_o$ in the suspension is uniform. In order for such a current to flow, the plates must be linked by a wire to complete the circuit. Under open-circuit conditions the current $i_o$ is therefore zero everywhere in the suspension. Thus equations (6) gives $$\alpha \nabla p_o = -K^* \underline{E}_o$$

where, for simplicity the suspension is taken to be isotropic. Integrating this result across the plates, it is found that $$\alpha \Delta P = K^* \Delta \psi$$

Thus if $K^*$ has been determined from a conductivity measurement, $\alpha$ can be obtained from the measurement of $\Delta P$ and $\Delta \psi$.

Alternatively, if the two plates are short circuited the electric field in the suspension will be zero, and (6) reduces to $$\underline{i}_o = \alpha \nabla p_o,$$

for an isotropic suspension. Integrating across the plates and using the fact that $\underline{i}_o$ is uniform it is found that $$\alpha = \frac{I_o h}{A \Delta P}$$

where A is the plate area, and $I_o e^{iwt}$ is the current passing between the plates. Thus by measuring the pressure difference and short-circuit current it is possible to determine without the need for a conductivity measurement.

The mathematical formula for obtaining $\underline{\alpha}$ for a general device is derived with the aid of the result $$\nabla \cdot \underline{i}_o = 0,$$

which holds everywhere in the suspension. Integrating equation (6) over the volume v of the suspension within the cell, and using the above identity, it is found that $$\int_A \underline{x} \underline{i}_o \cdot \underline{n} dA = \underline{\underline{\alpha}} \int_A p_o \underline{n} dA - \underline{\underline{K}}^* \int_A \psi \underline{n} dA, \quad (8)$$

where Z denotes the surface of v and $\underline{n}$ is the unit normal directed outwards from v. $\underline{x}$ is the position vector to the surface from an arbitrary point in the suspension, and $\psi e^{iwt}$ is the electrical potential.

From equation (8) it can be seen that components of $\underline{\underline{\alpha}}$ can be determined if $\underline{i}_o \cdot \underline{n}$, $p_o$ and $\psi$ are known over the surface of v. In the parallel plate device referred to above, either $\underline{i}_o \cdot \underline{n}$ (open-circuit) or $\psi$ (short-circuit) were set to zero, and the other two quantities measured.

As mentioned in §2, it is envisaged that the devices described here would make measurements over a range of frequencies appropriated to the expected particle size range.

Previous known devices are manufactured by Matec Instruments, Warwick, R.I., U.S.A. and Pen Kem, Inc., Bedford Hills, N.Y., U.S.A. The Matec device measures sound waves generated by electric fields, and electric fields generated by sound waves at about 1 MHz, in a parallel plate cell. The device measures the potential, but not the pressure difference across the cell. It is therefore not suited to the direct determination of $\underline{\underline{\alpha}}$.

The Pen-Kem instrument measures the potential difference between two electrodes caused by the generation of sound waves at around 200 kHz. The device also measures the pressure at a point some distance away from the electrodes. As it is not possible to directly determine the pressure difference between the electrodes from this single pressure measurement, this device is also unsuited to the direct determination of $\underline{\underline{\alpha}}$.

Apparatus according to the present invention measures the interaction of sound waves and electric fields over a range of frequencies, and comprises means to convert the information so obtained to provide a direct measurement of electrophoretic mobility, from which particle size and zeta potential can be inferred.

Although the invention has been described above with reference to examples and to preferred embodiments, it will be appreciated that the invention may be embodied in other forms or carried out in other ways without departing from the spirit or essential characteristics thereof. The above description is therefore to be considered in all respects, illustrative and not restrictive, and all changes which come within the meaning and range of equivalency are intended to be embraced therein.

I claim:

1. A method for determining the particle charge and size distribution of particles in suspensions of arbitrary concentration in a fluid medium, comprising:
   applying at least one of an unsteady electric field of at least two different frequencies and an unsteady mechanical force of at least two different frequencies to the suspension to accelerate the particles;
   measuring a resulting acoustic wave generated by the particles as a result of the application at each frequency of unsteady electric field, or a resulting electrical response generated by the particles as a result of the application at each frequency of unsteady mechanical force;
   determining the frequency dependent electrophoretic mobility of the particles from the measured acoustic wave or electrical response at each of the applied frequencies; and
   calculating the particle size and charge distribution from the frequency dependent electrophoretic mobility.

2. The method of claim 1 including the step of selecting the appropriate frequencies from an expected particle size range.

3. The method of claim 1, wherein the frequency dependent electrophoretic mobility is determined by applying an unsteady electric field to the suspension and measuring the resulting acoustic wave.

4. The method of claim 1, wherein the frequency dependent electrophoretic mobility is determined by applying an unsteady mechanical force and measuring the resulting electrical current.

5. The method of claim 1, wherein the frequency dependent electrophoretic mobility is determined by applying an unsteady mechanical force and measuring the resulting electrical voltage.

6. The method of claim 3, wherein the applied electric field is sinusoidal and the amplitude and phase of the frequency dependent electrophoretic mobility is calculated from the measurement of the amplitude and phase of the acoustic wave relative to the amplitude and phase of the applied electric field.

7. The method of claim 4, wherein the applied mechanical force is sinusoidal and the amplitude and phase of the frequency dependent electrophoretic mobility is calculated from the measurement of the amplitude and phase of the currents or voltages relative to the amplitude and phase of the applied mechanical force.

8. The method of claim 1, wherein the fluid is a liquid.

9. A method for determining the particle charge and size distribution of particles in suspensions of arbitrary concentration in a fluid medium, comprising:
   applying an unsteady electric field of at least two different frequencies to the suspension to accelerate the particles;
   measuring a resulting acoustic wave generated by the particles as a result of the application at each frequency of unsteady electric field;
   determining the frequency dependent electrophoretic mobility of the particles from the measured acoustic wave at each of the applied frequencies; and
   calculating the particle size and charge distribution from the frequency dependent electrophoretic mobility.

10. A method for determining the particle charge and size distribution of particles in suspensions of arbitrary concentration in a fluid medium, comprising:
   applying an unsteady mechanical force of at least two different frequencies to the suspension to accelerate the particles;
   measuring a resulting electrical response generated by the particles as a result of the application at each frequency of unsteady mechanical force;
   determining the frequency dependent electrophoretic mobility of the particles from the measured electrical response at each of the applied frequencies; and
   calculating the particle size and charge distribution from the frequency dependent electrophoretic mobility.

* * * * *